US010722750B2

(12) United States Patent
Martikka et al.

(10) Patent No.: US 10,722,750 B2
(45) Date of Patent: Jul. 28, 2020

(54) METHOD AND APPARATUS FOR DETERMINING EFFECT OF TRAINING ON IMPROVING FITNESS

(71) Applicant: SUUNTO OY, Vantaa (FI)

(72) Inventors: Mikko Martikka, Vantaa (FI); Erik Lindman, Vantaa (FI); Terho Lahtinen, Vantaa (FI); Michael Miettinen, Vantaa (FI)

(73) Assignee: Amer Sports Digital Services Oy, Vantaa (FI)

(*) Notice: Subject to any disclaimer, the term of this patent is extended or adjusted under 35 U.S.C. 154(b) by 486 days.

(21) Appl. No.: 13/832,001

(22) Filed: Mar. 15, 2013

(65) Prior Publication Data

US 2014/0018945 A1 Jan. 16, 2014

Related U.S. Application Data

(60) Provisional application No. 61/691,277, filed on Aug. 21, 2012.

(30) Foreign Application Priority Data

Jul. 10, 2012 (FI) ..................................... 20125787
Aug. 21, 2012 (GB) ..................................... 1214844

(51) Int. Cl.
*A63B 24/00* (2006.01)
*A61B 5/22* (2006.01)
(Continued)

(52) U.S. Cl.
CPC .......... *A63B 24/0062* (2013.01); *A61B 5/222* (2013.01); *G06Q 50/22* (2013.01);
(Continued)

(58) Field of Classification Search
CPC ..... A63B 24/00; A63B 24/0062; A61B 5/222; A61B 5/0006; G06Q 50/22
(Continued)

(56) References Cited

U.S. PATENT DOCUMENTS 5,435,315 A 7/1995 McPhee et al.
6,305,943 B1* 10/2001 Pougatchev ........... A61B 5/486
434/238
(Continued)

FOREIGN PATENT DOCUMENTS

EP 1897598 A1 3/2008
EP 2371278 A1 10/2011
(Continued)

OTHER PUBLICATIONS

EPOC Based Training Effect Assessment, Firstbeat Technologies Ltd., 2007.

*Primary Examiner* — William H McCulloch, Jr.
*Assistant Examiner* — Ankit B Doshi
(74) *Attorney, Agent, or Firm* — Laine IP Oy

(57) ABSTRACT

The present disclosure concerns determining physiological training effect of a physiological performance of a person by monitoring the performance using one or more performance-monitoring means in order to obtain performance data, and, according to one aspect of the invention, determining, using computing means capable of utilizing the performance data, a third training effect parameter describing a third physiological effect of the performance using a third determination method, the third physiological effect being a combination effect of the first and second physiological effects which are different from each other and are descriptive of different physiological effects of training, such as homeostatic disturbance and cumulative physiological load, respectively.

20 Claims, 2 Drawing Sheets

(51) Int. Cl.
*G06Q 50/22* (2018.01)
*A61B 5/11* (2006.01)
*A61B 5/024* (2006.01)
*A61B 5/00* (2006.01)

(52) U.S. Cl.
CPC ......... *A61B 5/0006* (2013.01); *A61B 5/02438* (2013.01); *A61B 5/11* (2013.01)

(58) Field of Classification Search
USPC .............................. 700/91; 463/20, 25, 30
See application file for complete search history.

(56) References Cited

U.S. PATENT DOCUMENTS

| | | | |
|---|---|---|---|
| 7,840,346 B2* | 11/2010 | Huhtala | A63B 24/0062 |
| | | | 701/439 |
| 2006/0004265 A1* | 1/2006 | Pulkkinen | A61B 5/0205 |
| | | | 600/300 |
| 2006/0032315 A1 | 2/2006 | Saalastic et al. | |
| 2006/0079800 A1* | 4/2006 | Martikka | A61B 5/0488 |
| | | | 600/546 |
| 2007/0232455 A1 | 10/2007 | Hanoun | |
| 2008/0119329 A1* | 5/2008 | Punkka | A61B 5/0535 |
| | | | 482/8 |
| 2009/0069156 A1 | 3/2009 | Kurunmäki et al. | |
| 2010/0037753 A1* | 2/2010 | Wagner | A61B 5/0205 |
| | | | 84/612 |
| 2016/0015308 A1* | 1/2016 | Kirenko | A61B 5/721 |
| | | | 600/301 |

FOREIGN PATENT DOCUMENTS

| | | |
|---|---|---|
| GB | 2443935 A | 5/2008 |
| WO | WO2008003830 A1 | 1/2008 |

* cited by examiner

METHOD AND APPARATUS FOR DETERMINING EFFECT OF TRAINING ON IMPROVING FITNESS

FIELD OF THE INVENTION

The invention relates to monitoring of physical performances. In particular, the invention relates to determining a training effect by monitoring intensity of the performance.

BACKGROUND OF THE INVENTION

Determining training effect (TE) by estimating Excess Post-Exercise Oxygen Consumption (EPOC) and activity class of a person is well-known prior art (see for example "*EPOC Based Training Effect Assessment*", White paper by Firstbeat Technologies Ltd., February 2007). EPOC measures the quantity of exercise-induced disturbance of body's homeostasis using heart beat measurements, whereas TE indicates the effect of a single exercise session on improvement of cardiorespiratory fitness and fatigue resistance during a prolonged exercise. Activity class is an index which describes the activity level of the person and is used to individualize the determination of TE. Activity class is typically determined based on the classification of Shvartz & Reibold in 1990.

The method to assess TE as described in the above-references publication is commonly used in wearable sports monitoring devices, such as wrist-worn sports monitors.

The known method suffers from some disadvantages. First, it has been noted that the TE determined during sports performances with a certain type of intensity profile does not correspond to the actual physiological effect achieved. For example, in the case of an exercise with a high intensity period in the beginning and a constant lower intensity period in the end, the TE has been found not to change during the constant intensity period although the person feels that the training is still effective.

Second, the TE may not reflect the true physiological effect in the case of very long training sessions. For example, during a long low-intensity exercise, a user may not see the TE rise significantly although the stressfulness felt during the exercise would be relatively high.

Third, the TE determination during discontinuous training sessions, i.e. sessions with pauses, is not reliable.

Fourth, the TE does not take into account base endurance of an individual in all circumstances. Although common TE calculation methods utilize activity class given as an index number, the result may not be truthful, since there are many personal factors affecting the base endurance that cannot be fully described by a simple activity class index. These include for example trajectories and economy of movements and habituation to stress. The latter includes a plurality of sub-factors comprising for example cell metabolism, number of mitochondria, capability of cells to produce ATP, state of development of capillaries, hormonal factors, and capability of heart to circulate blood.

On the basis of the above, there exists a need for improved methods and apparatuses to estimate the effect of training in improving the fitness of individuals.

SUMMARY OF THE INVENTION

It is an aim of the invention to respond to the abovementioned need and to provide a method and apparatus capable of more reliably indicating the effect of training in improving fitness.

The aim is achieved by the invention as defined in the independent claims.

Advantageous embodiments are defined in the dependent claims.

According to one aspect, the invention provides a method of determining physiological training effect of a physiological performance of a person on improving his/her fitness, the method comprising
monitoring the performance using one or more performance-monitoring means comprising at least heartbeat monitoring means, in order to obtain performance data,
determining, using computing means capable of utilizing the performance data,
a first training effect parameter describing a first physiological effect (such as homeostatic disturbance) of the performance using a first determination method, and
a second training effect parameter describing a second physiological effect (such as cumulative physiological load) of the performance using a second determination method, and
storing and/or displaying the first and second training effect parameters on storage and/or display means, respectively.

According to another aspect, the method comprises
monitoring the performance using one or more performance-monitoring means comprising at least heartbeat monitoring means in order to obtain performance data,
determining, using computing means capable of utilizing the performance data, a third training effect parameter describing a third physiological effect of the performance using a third determination method, the third physiological effect being a combination effect of the first and second physiological effects which are different from each other and are descriptive of different physiological effects of training (such as homeostatic disturbance and cumulative physiological load, respectively),
storing and/or displaying the third training effect parameter on storage and/or display means, respectively.

It should be noted that the explicit calculation of the first and second training effect parameters can be carried out, but is by no means necessary, for being able to calculate the third training effect parameter.

According to one embodiment, the method is a combination of both of the above main aspects, in which case all three training effect parameters are determined and stored and/or displayed.

According to one embodiment, the performance data and performance-monitoring means used for estimating the oxygen intake comprise interbeat interval data and heartbeat monitoring means, respectively.

According to one embodiment, the method further comprises determining a third training effect parameter describing the cumulative physiological training effect of the performance. The cumulative training effect is frequently referred to as totalTE (total training effect) below. The third training effect parameter is preferably calculated using said first and second training effect parameters, but it may also be calculated directly on the basis of the performance data using a third determination method.

According to one embodiment, the first physiological effect of the performance correlates with maximum stress experienced by the person during the performance. The stress is caused by the homeostatic disturbance of the performance on the person's body, and it correlates with maximal cardio-respiratory load experienced by the person during the performance. In other words, the first training effect parameter is descriptive of the effect of the performance on the person's maximal aerobic capacity or, in more common terms, peak fitness. For this reason, the first training effect parameter is referred to as peakTE (peak training effect) below.

According to one embodiment, the maximum stress, i.e. homeostatic disturbance, is determined by estimating oxygen intake during or after the performance, for example by calculating Excess Post-Exercise Oxygen Consumption (EPOC) or using any a corresponding oxygen intake model yielding an oxygen intake-dependent parameter. According to one embodiment, the performance data comprises interbeat interval data and the performance-monitoring means comprise heartbeat monitoring means.

According to one embodiment, the second determination method comprises estimating the cumulative physiological load of the performance. In other words, the second training effect parameter, also referred to as baseTE (base training effect) is a cumulative intensity parameter.

The cumulative physiological load can be determined in various ways. According to one embodiment, the same heartbeat monitoring means that are used for determining peakTE, are used for determining baseTE. In alternative solutions, the intensity estimated based on energy consumption data measured using energy consumption monitoring means, position or velocity data measured using a positioning sensor and/or velocity sensor, acceleration data measured using an acceleration sensor, or power data measured using a power output sensor. Also a combination of any of the above methods can be used.

According to one embodiment, the second determination method utilizes a formula which weights at least one intensity range of the performance compared with at least one other intensity range of the performance. The weighted range is preferably a range which improves base endurance. According to one embodiment, the weighting function is normally distributed around a selected intensity.

According to one embodiment, the second determination method comprises using heart beat frequency data measured using heartbeat monitoring means, and the second training effect parameter is determined as a cumulative heart rate frequency weighed with a non-constant weighing function.

According to one embodiment, the calculation of totalTE, irrespective of its calculation method, is adapted to provide a temporally monotonically increasing result for all kinds of temporal intensity profiles of performance. That is, the cumulative training effect never decreases during a single exercise. This corresponds to the true effect of training experienced by people doing sports.

Considerable advantages are obtained by means of the invention. In particular, as the invention adds one "dimension" more to the determination of training effect, it is able to give more truthful information on the real effect of training, which has been found not to be a "one-dimensional" quantity fundamentally. Thus, the information obtained by the person doing sports better corresponds to the actual physiological effect achieved.

Adding another dimension also allows the training effect to reflect the true physiological effect in the case of very long training sessions or discontinuous training sessions, in which previous methods have failed to produce reliable information.

In particular the various embodiments disclosed herein take into account the development of base endurance of an individual in all circumstances better than the previous methods trough evaluation of the intensity of training in addition to the maximum stress and/or oxygen intake.

DEFINITION OF TERMS

The first determination method is adapted to produce a first training effect parameter describing a first effect of performance. Preferably, the first effect of performance correlates with maximal stress, or more specifically, homeostatic disturbance and/or maximal cardio-respiratory load caused by the performance. In the detailed discussion below, the first effect of performance is referred to as peakTE.

The second determination method is adapted to produce a second training effect parameter describing a second effect of performance, the second training effect parameter and second effect being different that the first training effect parameter and first effect of performance, respectively. Preferably, the second effect of performance correlates with the cumulative physiological load of the performance. The second training effectparameter differs from the first training effect parameter discussed above in that it reflects the portion of the performance which improves base endurance of the person. Consequently, it has a stronger correlation with total energy consumption than the first training effect parameter. On the other hand, the first training effect parameter typically has a stronger correlation with peak EPOC than the second training effect parameter. In the detailed discussion below, the second effect of performance is referred to as baseTE.

The third determination method is adapted to produce a third training effect parameter describing a third effect of performance, the third training effect parameter being different that the first and second training effect parameters. The third effect of performance can be calculated using both the first and second effect of performance or directly from the performance data measured. Preferably, the third training effect is the cumulative training effect which is determinable based on both the first and second effect of performance. The third training effect parameter has a stronger correlation with recovery time than each the first and second training effect parameters considered alone. Recovery time describes the resting time needed by the person for fully recovering from the current exercise. In the detailed discussion below, the third effect of performance is referred to as totalTE.

Next, embodiments of the invention and advantages thereof are described with reference to the attached drawings.

DETAILED DESCRIPTION OF EMBODIMENTS

Figure 1:
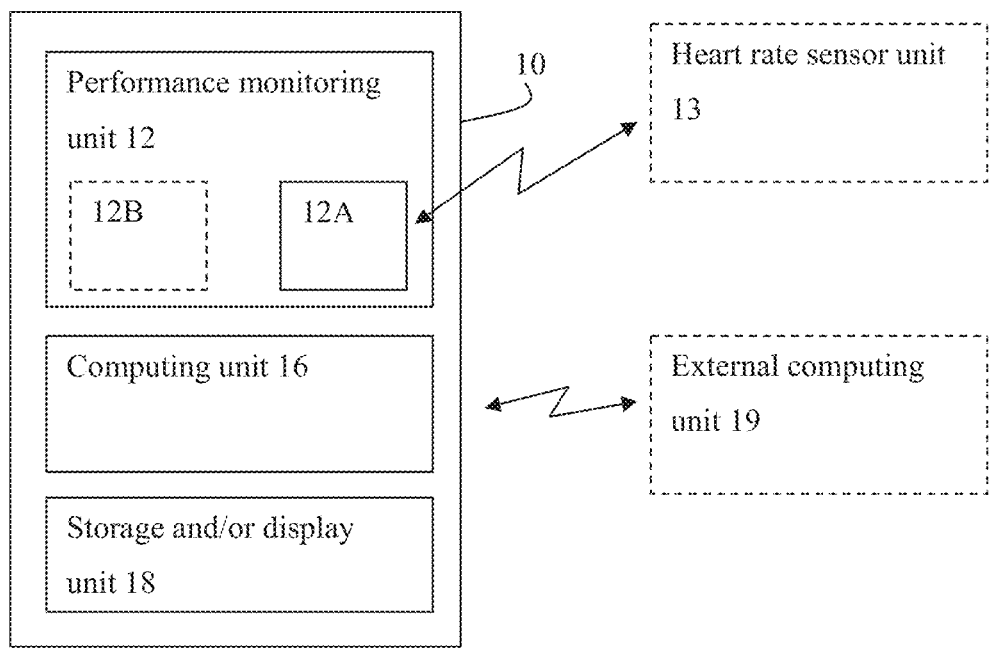
FIG. 1 shows a block diagram of a device according to one embodiment of the invention.

With reference to FIG. 1, the present invention can be carried out in a portable device 10. The device comprises a performance monitoring unit 12 having means for measuring or receiving heartbeat data of the user of the device. Typically, the unit 12 comprises a heartbeat data receiver 12A which is in wireless communication with a heart rate sensor unit 13, such as a heart rate belt. In addition, the performance monitoring unit may comprise one or more additional subunits 12B, which are adapted to measure or receive performance intensity data other than heartbeat data. The subunit(s) 12B may comprise e.g. acceleration measurement subunit, satellite positioning subunit, velocity measurement subunit or power measurement subunit.

The performance monitoring unit 12 is in functional connection with a computing unit 16 adapted to carry out the mathematical functions and/or algorithms required to obtain the training effect data desired. The results can be stored and/or displayed in a storage and/or display unit 18.

The device may also comprise means for communicating with an external computing unit 19, such as a computer.

Figure 2:
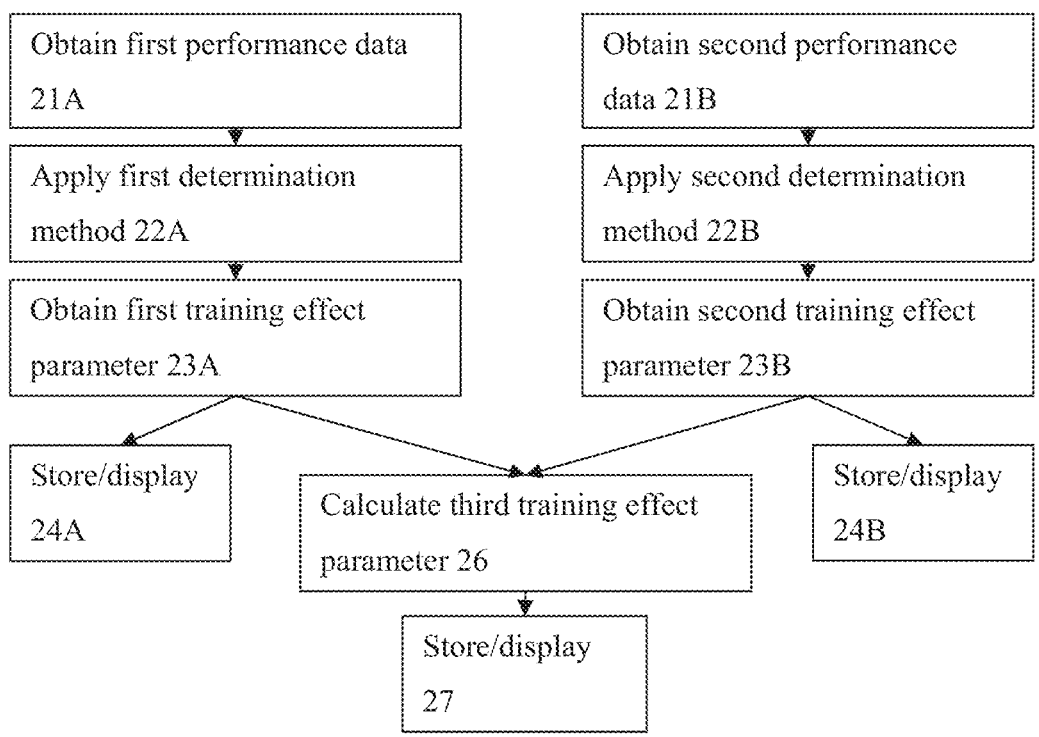
FIG. 2 shows a flow diagram of a method according to one embodiment of the invention.

With an additional reference to FIG. 2, the method may comprise as first steps 21A, 21B obtaining first and second performance data from the performance monitoring unit 12. The first and second performance data may be different or the same. Next, the computing unit 16 applies in the next steps 22A, 22B a first and second determination method on the first and second performance data, respectively. The first and second determination methods are different and reflect different "dimensions" of the physiological training. In steps 23A, 23B, the first and second training effect parameters are obtained as results of the first and second determination methods. In steps 24A, 24B, the parameters are stored on and/or displayed in the storage and/or display unit 18.

Next, the first and second training effect parameters are used to further calculate a third training effect parameter in step 26 in the computing unit 16.

Calculation of peakTE

According to one embodiment, peakTE is calculated using an estimated maximum stress experienced by the person during the performance. The maximum stress can be estimated based on heart rate measured.

Using mathematical expressions, $$\text{maxstress}=\text{maxstress}(\text{HRReff},\text{maxstress}), \text{ and}$$

$$\text{peakTE}=\text{peakTE}(\text{maxstress})$$

As reflected by the equation above, maxstress is preferably calculated using an interative algorithm taking into account the previously determined maxstress value.

HRReff refers to the person's effective heart rate calculated as the ratio of current heart rate to the difference between the maximum heart rate of the person and an recovery heart rate of the person (the difference thus depicting the available "heart rate reserve" at each moment of time). The recovery heart rate is an estimated heart rate level dynamically updated during the exercise and to which the heart rate of the person recovers in a certain time when the exercise is ended. For more information of the definitions used above, we refer to EP2371278.

According to one embodiment, the maximum stress is determined by estimating oxygen intake during or after the performance. A commonly known parameter correlating with oxygen intake is Excess Post-Exercise Oxygen Consumption (EPOC). However, any other parameter correlating with oxygen intake or, more generally, the stress state of the person, can be used instead of EPOC.

Calculation of baseTE

According to one embodiment, base TE is calculated as a weighed sum of the level of usage of heartbeat reserve.

Figure 4:
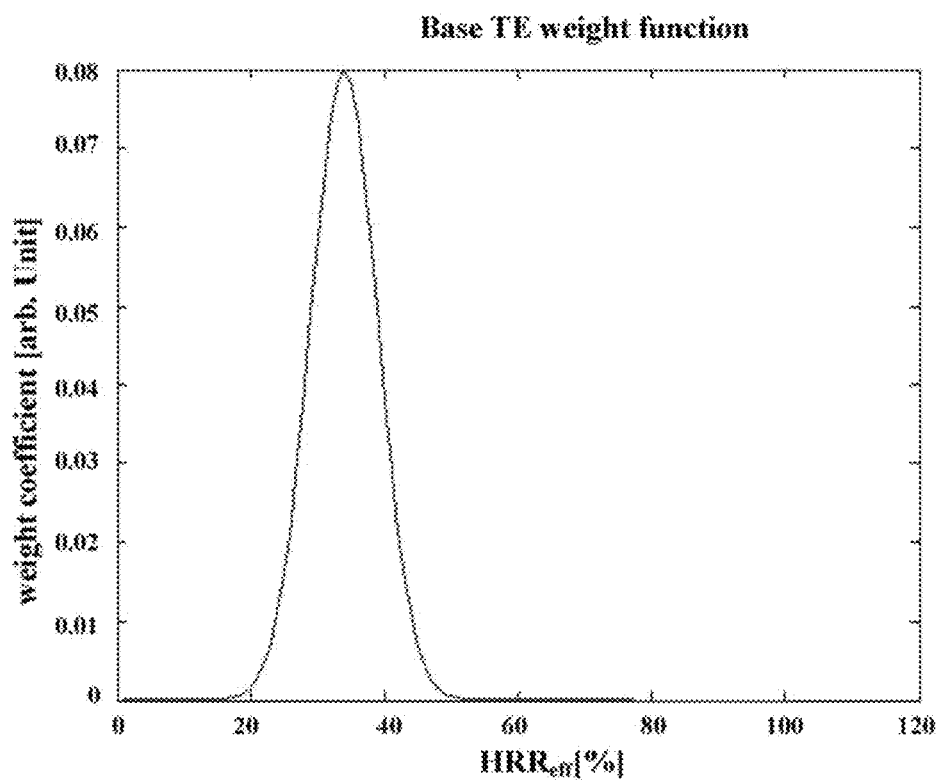
FIG. 4 shows an exemplary weighing function for the calculation of baseTE.

Using a Mathematical Expression $$\text{baseTE}=\text{baseTE}(\Sigma w_i*\text{HRReff}_i),$$

where i references to a series which is determined based on the heartbeat measurements at predetermined intervals, for example every ten seconds. $w_i$ is a weighing factor for each HRReff. An exemplary shape of the weighing function is shown in FIG. 4. The function is a normal distribution with an average of 33% of HRReff and standard distribution 5% of HRReff. The weighing function can be fixed, i.e. the same for all users, or alternatively adaptable or individually definable to correspond the personal properties of the person.

Calculation of totalTE

The calculation of totalTE can be implemented as a combination of the calculations of peakTE and baseTE.

Formulated mathematically, $$\text{totalTE}=\text{totalTE}(\text{maxstress},\Sigma ww_i*\text{HRReff}_i),$$

where $ww_i$ is again a weighing factor for each $\text{HRReff}_i$. However, it needs not be the same as in the direct baseTE calculation, i.e. it may be that $w_i \neq ww_i$.

Figure 3:
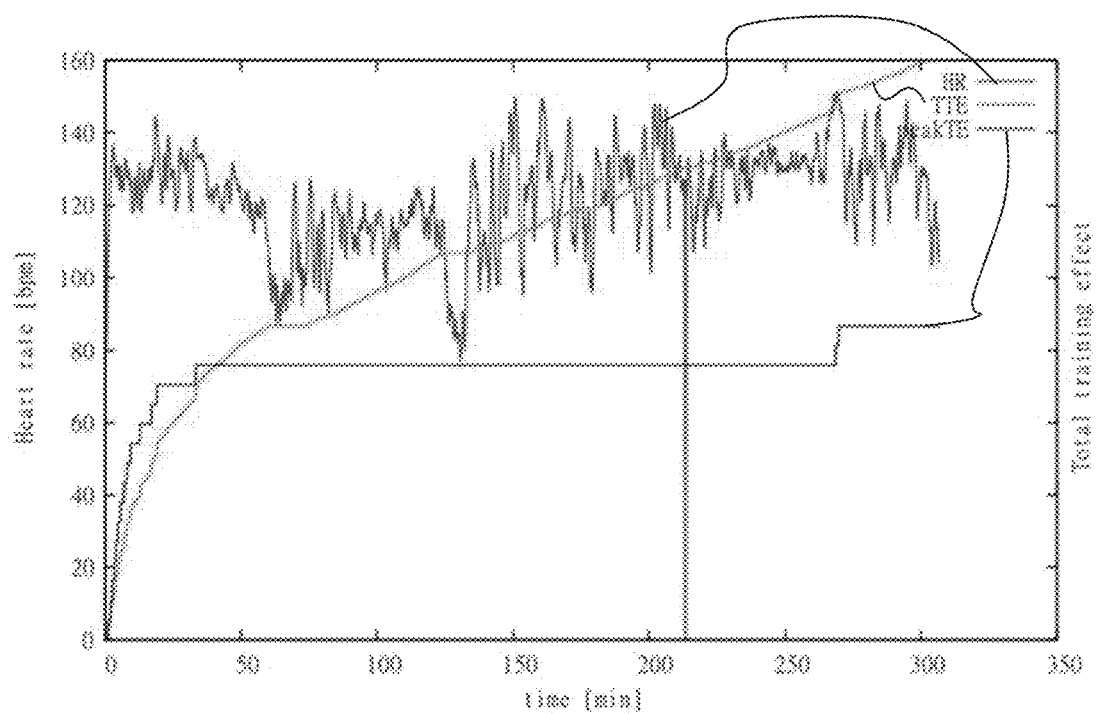
FIG. 3 show an exemplary graph of peakTE, totalTE (TTE) and heart rate (HR) vs. time.

FIG. 3 illustrates the calculation of peakTE and totalTE (TTE) parameters based on heart rate (HR) over time according to the above-described principles.

The invention claimed is:

1. A method of determining physiological training effect of a physiological performance of a person, comprising:
    monitoring the physiological performance of the person during an exercise session using one or more sensors including a heart rate sensor in order to obtain performance data;
    determining, using a computing unit capable of utilizing the physiological performance data,
        a first training effect parameter describing a first physiological peak training effect relating to an experienced maximum stress of the physiological performance using a first determination method, and
        a second training effect parameter describing a second physiological effect relating to cumulative physiological load of the physiological performance using a second determination method, and/or
        a third training effect parameter describing a third physiological effect of the physiological performance using a third determination method, the third physiological effect being a combination effect of the first physiological effect and second physiological effect and relating to recovery time; and
    storing the first and second training effect parameters on a storage unit and displaying at least one of said first, second and third training effects indicating the first, second and third effect of the exercise session on improvement of at least one of: cardiorespiratory fitness and fatigue resistance.

2. The method according to claim 1, wherein the third training effect parameter is determined and the third training effect parameter describes a cumulative physiological training effect of the physiological performance.

3. The method according to claim 1, wherein the third training effect parameter is calculated at least partly directly on the basis of the physiological performance data using the third determination method.

4. The method according to claim 1, wherein the first physiological peak training effect of the physiological performance correlates with homeostatic disturbance experienced by the person during the physiological performance.

5. The method according to claim 1, wherein the first determination method comprises estimating oxygen intake during or after the physiological performance for determining the first training effect parameter.

6. The method according to claim 5, wherein the physiological performance data and at least one sensor used for estimating the oxygen intake comprise interbeat interval data and a heartbeat sensor.

7. The method according to claim 1, wherein the second determination method comprises estimating the cumulative physiological load of the performance.

8. The method according to claim 1, wherein the second determination method comprises using at least one of the following as the physiological performance data and the one or more sensors: heart beat frequency data measured using the heart rate sensor, energy consumption data measured using an energy consumption sensor, position or velocity data measured using a positioning sensor and/or velocity sensor, acceleration data measured using an acceleration sensor, power data measured using a power output sensor.

9. The method according to claim 8, wherein the second determination method comprises using a combination of at least two physiological performance datas and the one or more sensors.

10. The method according to claim 1, wherein the second determination method is adapted to provide the second training effect parameter which is weighed on at least one intensity range of the play physiological performance relative to at least one other intensity range of the performance.

11. The method according to claim 8, wherein the second determination method comprises using heart beat frequency data measured using heartbeat sensor, and the second training effect parameter is determined as a cumulative heart rate frequency weighed with a non-constant weighing function.

12. The method according to claim 1, wherein the training effect parameters fulfill one or more of the following criteria: the second training effect parameter has a stronger correlation with total energy consumption than the first training effect parameter, the first training effect parameter has a stronger correlation with peak Excess Post-Exercise Oxygen Consumption (EPOC) than the second training effect parameter, the third training effect parameter has a stronger correlation with the recovery time than any of the first and second training effect parameters alone.

13. A device for determining physiological training effect of a physiological performance of a person, comprising
performance-monitoring means for providing physiological performance data from an exercise session,
computing means for treatment of the physiological performance data, the computing means being configured to determine
based on the physiological performance data, a first training effect parameter describing a first physiological effect relating to experienced maximum stress of the physiological performance using a first determination method, and
based on the physiological performance data, a second training effect parameter relating to cumulative physiological load of the performance using a second determination method; or
based on the physiological performance data and/or the first and second training effect parameters, a third training effect parameter describing a third physiological effect of the physiological performance using a third determination method, the third physiological effect being a combination effect of the first and second physiological effects and relating to recovery time,
means for displaying and/or storing the first and second, and/or the third training parameters, at least one of said first and second, and/or said third training parameters indicating the effect of the exercise session on improvement of cardiorespiratory fitness and/or fatigue resistance.

14. The device according to claim 13, wherein the computing unit is configured to calculate the third training effect parameter on the basis of the first and second training effect parameters, and the device comprises a display and a memory unit for displaying and/or storing the third training effect parameter, respectively.

15. The device according to claim 13, wherein the computing unit is configured to calculate the third training effect parameter at least partly directly from the physiological performance data and the device comprises a display and a memory unit for displaying and/or storing the third training effect parameter.

16. The device according to claim 13, wherein at least one heart rate sensor provides heart rate data and the first determination method is configured to estimate an oxygen intake during or after the physiological performance using heart interbeat interval invariability data, preferably by calculating Excess Post-Exercise Oxygen Consumption (EPOC).

17. The device according to claim 13, further comprising at least additional performance sensor selected from the group consisting of: one energy consumption monitoring sensor capable of providing energy consumption data; a positioning sensor and/or velocity sensor capable of providing position or velocity data; an acceleration sensor capable of providing acceleration data; and a power output sensor capable of providing power data, and the second determination method is configured to calculate at least one integral of said data for determining the second training effect parameter.

18. The device according to claim 17, wherein the second determination method is configured to calculate a weighed integral, the weighing being focused to at least one intensity range of the physiological performance relative to at least one other intensity range of the performance.

19. The method of claim 1, wherein the first determination method for the first physiological peak training effect includes calculating an estimated maximum stress experienced by the person during performance of the exercise session, and wherein the second determination method for a second physiological base training effect includes calculating the cumulative physiological load of the performance of the exercise session by a user.

20. The device of claim 13, wherein the first determination method of a first physiological peak training effect includes calculating an estimated maximum stress experienced by the person during performance of the exercise session, and wherein the second determination method for a second physiological base training effect includes calculating the cumulative physiological load of the performance of the exercise session by a user.

* * * * *